(12) United States Patent
Bacus et al.

(10) Patent No.: US 7,771,958 B2
(45) Date of Patent: Aug. 10, 2010

(54) METHOD FOR PREDICTING RESPONSE TO EPIDERMAL GROWTH FACTOR RECEPTOR-DIRECTED THERAPY

(75) Inventors: Sarah S. Bacus, Hinsdale, IL (US); David Haskett Lynch, Bainbridge Island, WA (US); Pamela Lockbaum, Moss Beach, CA (US); Gisela Schwab, Hayward, CA (US); Xiao-dong Yang, Palo Alto, CA (US)

(73) Assignee: Amgen Inc., Thousand Oaks, CA (US)

( * ) Notice: Subject to any disclaimer, the term of this patent is extended or adjusted under 35 U.S.C. 154(b) by 239 days.

(21) Appl. No.: 11/548,386

(22) Filed: Oct. 11, 2006

(65) Prior Publication Data

US 2007/0134252 A1 Jun. 14, 2007

Related U.S. Application Data

(62) Division of application No. 10/600,129, filed on Jun. 19, 2003.

(60) Provisional application No. 60/389,796, filed on Jun. 19, 2002.

(51) Int. Cl.
*G01N 33/574* (2006.01)
*G01N 33/567* (2006.01)
*G01N 33/577* (2006.01)

(52) U.S. Cl. .................. 435/7.23; 435/7.1; 435/7.21; 436/63; 436/64; 436/501

(58) Field of Classification Search .................. 435/7.1, 435/7.21, 7.23; 436/63, 64, 501
See application file for complete search history.

(56) References Cited

U.S. PATENT DOCUMENTS

| | | | |
|---|---|---|---|
| 5,726,023 A | 3/1998 | Cheever et al. | |
| 5,763,164 A | 6/1998 | Calenoff | |
| 5,770,195 A | 6/1998 | Hudziak et al. | |
| 5,869,445 A | 2/1999 | Cheever et al. | |
| 5,968,511 A * | 10/1999 | Akita et al. | 424/141.1 |
| 6,063,586 A * | 5/2000 | Grandis | 435/7.23 |
| 6,127,126 A | 10/2000 | Vogelstein et al. | |
| 6,235,883 B1 | 5/2001 | Jakobovits et al. | |

OTHER PUBLICATIONS

Esteva, F. J. et al., Pathology Oncology Research, 7(3): 171-177, 2001; abstract only.*
Accession No. P28482, Database PIR, (MK01_Human), Georgetown University, Washington, DC, Version 95, Feb. 26, 2008.*
Chow, N.-H. et al., Virchows Arch., 430(6): 461-466, 1997.*
Kong, A. et al., PLoS ONE, 3(8): e2881, 2008.*
Pinkas-Kramarski, R., et al., Oncogene, 16:1249-1258 (1998).
Hoffmann, M. et al. Cancer Immunol. Immunother. 47(3):167-175 (1998) (abstract only).
Alaoui-Jamali et al., "The role of ErbB-2 tyrosine kinase receptor in cellular intrinsic chemoresistance: mechanisms and implications," Biochem. Cell. Biol., 75:315-325, 1997.
Albanell et al., "Unraveling Resistance to Trastuzumab (Herceptin): Insulin-Like Growth Factor-I Receptor, a New Suspect," Journal of the National Cancer Institute, vol. 93(24):1830-31, 2001.
Altiok et al., "Heregulin Induces Phosphorylation of BRCA1 through Phosphatidylinositol 3-Kinase/AKT in Breast Cancer Cells," Journal of Biological Chemistry, 274(5):32274-32278, 1999.
Arteaga et al., "$p^{185c\text{-}erbB\text{-}2}$ Signaling Enhances Cisplatin-induced Cytotoxicity in Human Breast carcinoma Cells: Association between an Oncogenic Receptor Tyrosine Kinase and Drug-induced DNA Repair," Cancer Research, 54:3758-3765, 1994.
Arteaga et al., "The Epidermal Growth Factor Receptor: From Mutant Oncogene in Nonhuman Cancers to Therapeutic Target in Human Neoplasia," J Clinical Oncology, vol. 1999, 19(18s):32s-40s, 2001.
Bacus et al., "A Ligand for the erbB-2 oncogene Producet (gp30) Induces Differentiation of Human Breast Cancer Cells," Cell Growth & Diff., 3:401-411, 1992.
Bacus et al., "AKT2 is frequently upregulated in HER-2/neu-positive breast cancers and may contribute to tumor aggressiveness by enhancing cell survival," Oncogene, 21:3532-3540, 2002.
Bacus et al., "Neu Differentiation Factor (Heregulin) Induces Expression of Intercellular Adhesion Molecule 1: Implications for Mammary Tumors," Cancer Res. 53:5251-5261, 1993.
Bacus et al., "Potential Use of Image Analysis for the Evaluation of Cellular Predicting Factors for Therapeutic Response in Breast Cancers," Analytical and Quantitative Cytology and Histology 19:316-328 (1997).
Bargmann et al., "Multiple Independent Activations of the neu Oncogene by a Point Mutation Altering the Transmembrane Domain of p185," Cell, vol. 45:649-657, 1986.

(Continued)

*Primary Examiner*—Alana M. Harris
*Assistant Examiner*—Anne L Holleran
(74) *Attorney, Agent, or Firm*—Scott N. Bernstein

(57) ABSTRACT

This invention provides methods for determining or predicting response to cancer therapy in an individual.

14 Claims, 2 Drawing Sheets

OTHER PUBLICATIONS

Baselga et al., "Combined anti-EGF receptor and anti-HER2 receptor therapy in breast cancer: a promising strategy ready for clinical testing," Annuals of Oncology 13:8-9, 2002.
Baselga et al., "Receptor Blockade with Monoclonal Antibodies as Anti-Cancer Therapy," Pharmacol Ther 64:127-154, 1994.
Baselga, "Why the Epidermal Growth Factor Receptor? The Rationale for Cancer Therapy," The Oncologist 7(suppl 4):2-8 2002.
Basso et al, "Ansamycin antibiotics inhibit Akt activation and cyclin D expression in breast cancer cells that overexpress HER2," Oncogene, 21:1159-1166, 2002.
Bruns et al., "Blockade of the Epidermal Growth Factor Receptor Signaling by a Novel Tyrosine Kinase Inhibitor Leads to Apoptosis of Endothelial Cells and Therapy of Human Pancreatic Carcinoma," Cancer Research, 60:2926-2935, (2000).
Carpenter et al., "Epidermal Growth Factor," An. Review Biochem., 48:193-216, 1979.
Carraway et al., "The erbB3 Gene Product Is a Receptor for Heregulin," Journal Biological Chemistry, 269(19):14303-14306, 1994.
Carter et al, "Humanization of an anti-p185$^{HER2}$ antibody for human cancer therapy," Proc. Natl Acad Sci USA 89:4285-4289, 1992.
Chow et al., "Expression patterns of erbB receptor family in normal urothelium and transitional cell carcinoma, An immunohistochemical study", Virchows Arch (1997) 430:461-466.
Christensen et al, "High Levels of HER-2 Expression Alter the Ability of Epidermal Growth Factor Receptor (EGFR) Family Tyrosine Kinase Inhibitors to Inhibit EGFR Phosphorylation in Vivo," Clinical Cancer Research, vol. 7:4230-4238, 2001.
Ciardiello, et al., "A Novel Approach in the Treatment of Cancer: Targeting the Epidermal Growth Factor Receptor", Clinical Cancer Research 7:2958-2970, 2001.
Cobleigh et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," Journal of Clinical Oncology 17(9):2639-2648 (1999).
Coussens et al., "Tyrosine Kinase Receptor with Extensive Homology to EGF Receptor Shares Chromosomal Location with neu Oncogene," Science, 230(4730):1130-1139, 1985.
Database PIR, Accession No. P28482 (MK01_Human), Georgetown University, Washington, DC Version 95, Feb. 26, 2008.
Demitri et al.; "Efficacy and Safety of IMATINIB Mesylate in Advanced Gastrointestinal Stromal Tumors," New England Journal of Medicine 347(7):472-480 (2002).
Druker et al., "Efficacy and Safety of Specific Inhibitor of the BCR-ABL Tyrosine Kinase in Chronic Myeloid Leukemia," New England Journal of Medicine 344(14):1031-1037 (2001).
Erlichman et al., "the HER Tyrosine Kinase Inhibitor CI1033 Enhances Cytotoxicity of 7-Ethyl-10-hydroxycamptothecin and Topotecan by Inhibiting Breast Cancer Resistance Protein-mediated Drug Efflux," Cancer Research 61:739-748, 2001.
Esteva et al.; "Expression of erbB/HER receptors, heregulin and P38 in primary breast cancer using quantitative immunohistochemistry," Pathology Oncology Research 7(3):171-177 2001.
Fujimoto-Ouchi et al, "Antitumor activity of combinations of anti-HER-2 antibody trastuzumab and oral fluoropyrimidines capecitabine/5'-dFUrd in human breast cancer models," Cancer Chemother Pharmacol, 49:211-216, 2002.
Fujimura et al., "Selective Inhibition of the Epidermal Growth Factor Receptor by ZD1839 Decreases the Growth and Invasion of Ovarian Clear Cell Adenocarcinoma Cells," Clinical Cancer Research, vol. 8:2448-2454, 2002.
Fukazawa et al., "Tyrosine Phosphorylation of Cbl upon Epidermal Growth Factor (EGF) Stimulation and Its Association with EGF Receptor and Downstream Signaling Proteins," Journal of Biological Chemistry 271(24):14554-14559 (1996).
Hackel et al., "Epidermal growth factor receptors: critical mediators of multiple receptor pathways," Curr. Opin. Cell Biol. 11:184-189 (1999).

Hancock et al., "A Monoclonal Antibody against the c-erbB-2 Protein Enhances the Cytotoxicity of cis-Diamminedichloroplatinum against Human Breast and Ovarian Tumor Cell Lines," Cancer Research, 51:4575-4580, 1991.
Herbst et al., "IMC-C225, an anti-epidermal growth factor receptor monoclonal antibody, for treatment of head and neck cancer," Expert Opinion Biol. Ther. 1(4):719-732 2001.
Herbst et al., "Selective Oral Epidermal Growth Factor Receptor Tyrosine Kinase Inhibitor ZD1839 Is Generally Well-Tolerated and Has Activity in Non-Small-Cell Lung Cancer and Other Solid Tumors: Results of a Phase I Trial," Journal of Clincal Oncology, vol. 20(18):3815-3825, 2002.
Hidalgo et al, "Phase I and Pharmacologic Study of OSI-774, an epidermal Growth Factor Receptor Tyrosine Kinase Inhibitor, in Patients With Advanced Solid Malignancies," Journal of Clinical Oncology, vol. 19(13):3267-3279, 2001.
Holmes et al, "Identification of Heregulin, a Specific Activator of p185$^{erbB2}$," Science, 256(5060):1205-1210, 1992.
Huang et al., "Modulation of Radiation Response after Epidermal Growth Factor Receptor Blockade in Squamous Cell Carcinomas: Inhibition of Damage Repair, Cell Cycle Kinetics, and Tumor Angiogenesis," Clinical Cancer Res., vol. 7:2166-2174, 2000.
Hudziak et al., "p185$^{HER2}$ Monoclonal Antibody Has Antiproliferative Effects in Vitro and Sensitizes human Breast Tumor Cells to Tumor Necrosis Factor," Mol. Cell. Biol., 9(3):1165-1172, 1989.
Klapper et al., "A subclass of tumor-inhibitory monoclonal antibodies to ErbB-2/HER2 blocks crosstalk with growth factor receptors," Oncogene 14:2099-2109, 1997.
Klapper et al., "Tumor-inhibitory Antibodies to HER-2/ErbB-2 May Act by Recruiting c-Cbl and Enhancing Ubiquitination of HER-2," Cancer Research, 60:3384-3388, 2000.
Kraus et al., "Isolation and characterization of ERBB3, a third member of the ERBB / epidermal growth factor receptor family: Evidence for overexpression in a subset of human mammary tumors," Proc. Natl. Acad. Sci. USA, 86:9193-9197, 1989.
Lange et al., "Convergence of Progesterone and Epidermal Growth Factor Signaling in Breast Cancer," Journal of Biological Chemistry 273(47):31308-31316 (1998).
Liu et al., "Heregulin Regulation of Akt/Protein Kinase B in Breast Cancer Cells," Biochemical and Biophysical Research Communications, 261:897-903, 1999.
Mendelsohn & Baselga, "The EGF receptor family as targets for cancer therapy," Oncogene 19:6550-6565 (2000).
Mendelsohn, "The epidermal growth factor receptor as a target for therapy with antireceptor monoclonal antibodies," Seminars in Cancer Biology, vol. 1:339-344, 1990.
Moasser et al, "The Tyrosine Kinase Inhibitor ZA1839 ("Iressa") Inhibits HER2-driven Signaling and Suppresses the Growth of HER2-overexpressing Tumor Cells," Cancer Research, 61:7184-7188, 2001.
Munster et al., "Degradation of HER2 by Ansamycins Induces Growth Arrest and Apoptosis in Cells with HER2 Overexpression via a HER3, Phosphatidylinositol 3'-Kinase-AKT-dependent Pathway," Cancer Research 62:3132-3137, 2002.
Normanno et al, "Cooperative inhibitory effect of ZA1839 (Iressa) in combination with trastuzumab (Herceptin) on human breast cancer cell growth," Annals of Oncology, 13:65-72, 2002.
Olayioye et al., "ErbB-1 and ErbB-2 Acquire Distinct Signaling Properties Dependent upon Their Dimerization partner," Molecular and Cellular Biology 18(9):5042-5051 (1998).
Peles et al., "Cell-type specific Interaction of Neu differentiation factor (NDF/heregulin) with Neu/HER-2 suggests complex ligand—receptor relationships," EMBO Journal; 12(3):961-71, 1993.
Peles et al., "Isolation of the Neu/HER-2 Stimulatory Ligand: A 44 kd Glycoprotein That Induces Differentiation of Mammary Tumor Cells," Cell, 69:205-216, 1992.
Pietras et al., "Antibody to HER-2/neu receptor blocks DNA repair after cisplatin in human breast and ovarian cancer cells," Oncogene, 9:1829-1838, 1994.
Pinkas-Kramarski et al., "Brain neurons and glial cells express Neu differentiation factor / heregulin: A survival factor for astrocytes," Proc. Natl. Acad. Sci. USA, 91:9387-9391, 1994.

Pinkas-Kramarski et al., "Neu Differentiation Factor/Neuregulin Isoforms Activate Distinct Receptor Combinations," The Journal of Biological Chemistry, vol. 271(32):19029-19032, 1996.

Pinkas-Kramarski et al., "The oncogenic ErbB-2/ErbB-3 heterodimer is a surrogate receptor of the epidermal growth factor and betacellulin," Oncogene, 16:1249-1258, 1998.

Plowman et al., "Heregulin Induces tyrosine phosphorylation of HER4/p180$^{erbB4}$," Nature, 366:473-475, 1993.

Sachs et al., "Cell Differentiation and Bypassing of Genetic Defects in the Suppression of Malignancy," Cancer Res., 47:1981-1986, 1987.

Semba et al., "A v-erbB-related protooncogene, c-erbB-2, is distinct from the c-erbB-1/epidermal growth factor-receptor gene and is amplified in a human salivary gland adenocarcinoma," Proc. Natl. Acad. Sci., 82:6497-6501, 1985.

Shak, "Overview of the Trastuzumab (Herceptin) Anti-HER2 Monoclonal Antibody Clinical Program in HER2- Overexpressing Metastatic Breast Cancer," Seminars in Oncology, vol. 26(4, Suppl 12):71-77, 1999.

Shin, et al., "Epidermal Growth Factor Receptor-targeted Therapy with C225 and Cisplatin in Patients with Head and Neck Cancer", Clinical Cancer Research 7:1204-1213, 2001.

Slamon et al., "Human Breast Cancer: Correlation of Relapse and Survival with Amplification of the HER-2/neu Oncogene," Science, 235(4785):177-182, 1987.

Sliwkowski et al, "Nonclinical Studies Addressing the Mechanism of Action of Trastuzumab (Herceptin)," Seminars in Oncology, 26(4, Suppl 12):60-70, 1999.

Soukos, et al., "Epidermal Growth Factor Receptor-targeted Immunophotodiagnosis and Photoimmunotherapy of Oral Precancer in Vivo", Cancer Research 61:4490-4496, 2001.

Stancovski et al., "Mechanistic aspects of the opposing effects of monoclonal antibodies to the ERBB2 receptor on tumor growth," Proc Natl Acad Sci USA 88:8691-8695, 1991.

Tagliabue et al., "Selection of monoclonal antibodies which induce internalization and phosphorylation of p185$^{HER2}$ and growth inhibition of cells with HER2/NEU gene amplification," Int. J. Cancer, 47:933-937, 1991.

Tzahar et al., "A Hierarchical Network of Interreceptor Interactions Determines Signal Transduction by Neu Differentiation Factor/Neuregulin and Epidermal Growth Factor," Molecular and Cellular Biology 16(10):5276-5287 (1996).

Tzahar et al., "ErbB-3 and ErbB-4 Function as the Respective Low and High Affinity Receptors of All Neu Differentiation Factor/Heregulin Isoforms," Journal of Biological Chemistry, 269(40):25226-25233, 1994.

Vogel et al., "Efficacy and Safety of Trastuzumab as a Single Agent in First-Line Treatment of HER2- Overexpressing Metastatic Breast Cancer," Journal of Clinical Oncology, vol. 20(3):719-726, 2002.

Vogel et al., "First-Line Herceptin® Monotherapy in Metastatic Breast Cancer," Oncology, 61(suppl 2):37-42, 2001.

Xia et al. "Anti-tumor activity of GW572016: a dual tyrosine kinase inhibitor blocks EGF activation of EGFR/erbB2 and downstream Erk1/2 and AKT pathways," Oncogene 21:6255-6263 (2002).

Xia et al., "Combination of EGFR. HER-2/neu, and Her-3 Is a Stronger Predictor for the Outcome of Oral Squamous Cell Carcinoma Than Any Individual Family Members," Clinical Cancer Research 5:4164-4174 1999.

Xing et al., "The Ets protein PEA3 suppresses HER-2/neu overexpression and inhibits tumorigenesis," Nature Med., 6(2):189-195, 2000.

Yang et al., "Eradication of Established Tumors by a Fully Human Monoclonal Antibody to the Epidermal Growth Factor Receptor without Concomitant Chemotherapy," Cancer Research 59(6):1236-1243 (1999).

Yang X et al., "Development of ABX-EGF, a fully human anti-EGF receptor monoclonal antibody, for cancer therapy," Crit Rev Oncol Hemato 38(1):17-23 (2001).

Ye et al., "Augmentation of a humanized Anti-HER2 mAb 4D5 induced growth inhibition by a human-mouse chimeric anti-EGF receptor mAb C225," Oncogene, 18:731-738, 1999.

* cited by examiner

Patient 3019
Example of Elevated HER1 and pERK with low HER3

| marker | level |
|--------|-------|
| EGFR   | 18    |
| pEGFR  | 14    |
| HER2   | 0     |
| HER3   | 2     |
| pERK   | 924   |

Example of Sample with Elevated HER1, HER3, and pERK

| marker | level |
|--------|-------|
| EGFR   | 28    |
| pEGFR  | 23    |
| HER2   | 5     |
| HER3   | 15    |
| pERK   | 600   |

1

METHOD FOR PREDICTING RESPONSE TO EPIDERMAL GROWTH FACTOR RECEPTOR-DIRECTED THERAPY

This application is a divisional application of application Ser. No. 10/600,129, Jun. 19, 2003, which claims the benefit of U.S. Provisional Application Ser. No. 60/389,796, filed Jun. 19, 2002.

BACKGROUND OF THE INVENTION

1. Field of the Invention

This invention relates to methods for predicting the response to cancer therapy in an individual.

2. Background of the Invention

Cellular growth and differentiation processes involve growth factors that exert their actions through specific receptors expressed in the surfaces of responsive cells. Ligands binding to surface receptors, such as those that carry an intrinsic tyrosine kinase activity, trigger a cascade of events that eventually lead to cellular proliferation and differentiation (Carpenter et al., Biochem., 48: 193-216, 1979; Sachs et al., Cancer Res., 47: 1981-1986, 1987). Receptor tyrosine kinases can be classified into several groups on the basis of sequence similarity and distinct features. One of these groups includes the epidermal growth factor receptor family, which included erbB-1 (EGFR or HER-1) (Carpenter et al., Biochem., 48: 193-216, 1979); erbB-2 (HER-2/neu) (Semba et al., Proc. Natl. Acad. Sci., 82: 6497-6501, 1985; Coussens et al., Science, 230: 1130-1139, 1985, Bargmann et al., Cell, Vol. 45, 649-657, 1986); erbB-3 (HER-3) (Kraus et al., Proc. Natl. Acad. Sci., 86: 9193-9197, 1989; Carraway et al., R. A. J. Biol. Chem., 269: 14303-14306, 1994), and erbB-4 (HER-4) (Plowman et al., Nature, 366: 473-475, 1993; Tzahar et al., Biol. Chem., 269: 25226-25233, 1994).

As an example of a ligand that can bind to surface receptors, NDF (neu differentiation factor)/Heregulin is a receptor tyrosine kinase ligand that can stimulate the tyrosine phosphorylation of erbB-2 through heterodimerization with its receptors erbB-3 or erbB-4 (Peles, et al., Cell, 69:205-216, 1992, Peles, et al., EMBO J. March;12(3):961-71, 1993; Holmes et al, Science, 256:1205-1210, 1992. Tzahar et al., Biol. Chem., 269: 25226-25233, 1994; Plowman et al., Nature, 366: 473-475, 1993; Pinkas-Kramarski et al., Proc. Natl. Acad. Sci., 91:9387-9391, 1994; Pinkas-Kramarski et al., The Journal of Biological Chemistry, Vol. 271, No. 32: 19029-19032, 1996; Pinkas-Kramarski et al., Oncogene, 16, 1249-1258, 1998.). Depending on the cell line studied, NDF/Heregulin can either elicit a growth arrest and differentiation phenotype, resulting in morphological changes, induction of lipids, and expression of intracellular adhesion molecule-1, or induce a mitogenic response (Holmes et al., Science, 256: 1205-1210, 1992; Peles et al., Cell, 69:205-216, 1992; Bacus et al., Cancer Res. 53:5251-5261, 1993).

Activation of erbB receptor heterodimers is coupled to and stimulates downstream MAPK-Erk1/2 and PI3K-AKT growth and survival pathways whose deregulation in cancer has been linked to disease progression and refractoriness to therapy (Olayioye, M. A., et al., Mol. Cell. Biol. 18, 5042-5051 (1998), Fukazawa, T., et al., J. Biol. Chem. 271, 14554-14559 (1996), Hackel, P. O., et al., Curr. Opin. Cell Biol. 11, 184-189 (1999); Tzahar, E., et al., Mol. Cell. Biol. 16, 5276-5287 (1996); Lange, C. A., et al., J. Biol. Chem. 273, 31308-31316 (1998). For example, HER-3 is a major docking site for phoshoinositide-3-kinase (PI3K). In addition, NDF/Heregulin stimulation causes activation of the PI3K pathway and phosphorylation of AKT (Altiok et al., J. Biol. Chem., 274, 32274-32278, 1999; Liu et al., Res. Comm., 261, 897-903, 1999; Xing et al., Nature Med., 6, 189-195, 2000). These observations implicate PI3K/AKT in the signaling cascade that results from HER-3 heterodimerization with overexpressed HER-2/neu receptors in breast cancer cells; activation of PI3K/AKT promote cell survival and enhanced tumor aggressiveness (Shak, Semin. Oncol., Suppl 12:71-77, 1999; Huang et al., Clinical Cancer Res., Vol. 7: 2166-2174, 2000). In addition, AKT2 was reported to be activated and overexpressed in HER-2/neu-overexpressing breast cancers (Bacus et al., Oncogene, 21: 3532-3540, 2002).

Most tumors of epithelial origin express multiple erbB (HER) receptors and co-express one or more EGF-related ligands suggesting that autocrine receptor activation plays a role in tumor cell proliferation. Because these ligands activate different erbB/HER receptors, it is possible that multiple erbB receptor combinations might be active in a tumor, a characteristic that could influence its response to an erbB-targeted therapeutic. For example, erbB-2/HER-2 is overexpressed in 20 to 30% of all breast cancers, and its overexpression is associated with poor prognosis, suggesting that it could be used as a target for anti-tumor agents (Slamon et al., Science, 235: 177-182, 1987; Tagliabue et al., Int. J. Cancer, 47: 933-937, 1991; Hudziak et al., Mol. Cell. Biol., 9: 1165-1172, 1989). Studies have shown that in erbB-2 overexpressing breast cancer cells, treatment with antibodies specific to HER-2/erbB-2 in combination with chemotherapeutic agents (e.g., cisplatin, doxoubicin, taxol) elicits a higher cytotoxic response than treatment with chemotherapy alone (Hancock et al., Cancer Res., 51: 4575-4580, 1991; Arteaga et al., Cancer, 54:3758-3765, 1994; Pietras et al., Oncogene, 9: 1829-1838, 1994). One possible mechanism by which HER-2/erbB-2 antibodies might enhance cytotoxicity to chemotherapeutic agents is through the modulation of the HER-2/erbB-2 protein expression, (Bacus et al., Cell Growth & Diff., 3: 401-411, 1992, Bacus et al., Cancer Res. 53:5251-5261, 1993; Stancovski et al., Proc Natl Acad Sci USA 88: 8691-8695, 1991; Klapper et al., Oncogene 14, 2099-2109, 1997, and Klapper et al., Cancer Res., 60: 3384-3388, 2000), or by interfering with DNA repair (Arteaga et al., Cancer, 54:3758-3765, 1994, and Arteaga et al., J Clinical Oncology, Vol. 19, No 18s, 32s-40s, 2001; Pietras et al., Oncogene, 9: 1829-1838, 1994).

Because of the effect of anti-HER-2/erbB-2 antibodies on cellular growth, a number of approaches have been used to therapeutically target HER-2/erbB-2 or EGFR overexpressing cancers. For clinical use, one approach is to interfere with the kinase activity of the receptor by using inhibitors that block the nucleotide binding site of HER-2/neu or EGFR (Bruns, et al., Cancer Research, 60,2926-2935, (2000); Christensen, et al, Clinical Cancer Research, Vol. 7, 4230-4238, 2001, Erlichman, et al., Cancer Research 61, 739-748, 2001, Fujimura, et al., Clinical Cancer Research, Vol. 8, 2448-2454, 2002; Herbst, et al., Journal of Clincal Oncology, Vol. 20, No. 18, 3815-3825, 2002; Hidalgo, et al, J. Clinical Oncology, Vol 19, No 13: pp 3267-3279, 2001; Moasser, et al., Cancer Res., 61: 7184-7188, 2001; Normanno, et al., Ann. of Oncol., 13: 65-72, 2002). A second approach is using ansamycins to influence the stability of HER2/neu receptors (Munster, et al., Cancer Research 62, 3132-3137, 2002; Basso et al, Oncogene, 21: 1159-1166, 2002). Another approach is the use of antibodies directed to various erbB receptors specifically EGFR or HER-2/neu (Alaoui-Jamali, et al Biochem. Cell. Biol., 75:315-325, 1997; Albanell, et al., J. National Cancer Institute, Vol 93, No. 24, 1830-31, 2001; Baselga, et al., Pharmacol Ther 64: 127-154, 1994 and Baselga, et al., Annuals of Oncology 13: 8-9, 2002; Mendelsohn, Seminars in Cancer Biology, Vol. 1, pp. 339-344, 1990). A number of monoclonal antibodies and small molecule, tyrosine kinase inhibitors targeting EGFR or erbB-2 have been developed. For example, HERCEPTIN® is approved for treating the 25% of women whose breast cancers overexpress erbB-2 protein or demonstrate erbB-2 gene amplification (Cobleigh, M. A., et al., *J. Clin. Oncol.* 17, 2639-2648 (1999)). Analysis of various antibodies to HER-2/neu has led to the identification of the murine monoclonal, 4D5. This antibody recognizes an extracellular epitope (amino acids 529 to 627) in the cysteine-rich II domain that resides very close to the transmembrane region. Treatment of breast cancer cells with 4D5 partially blocks NDF/heregulin activation of HER-2-HER-3 complexes, as measured by receptor phosphorylation assays. To allow for chronic human administration, murine 4D5 was humanized to generate HERCEPTIN® (trastuzumab) (Sliwkowski et al, Sem. in Oncol., 26:60-70, 1999; Ye et al., Oncogene, 18: 731-738, 1999; Carter et al, Proc. Natl. Acad Sci USA 89:4285-4289, 1992; Fujimoto-Ouchi et al, Cancer Chemother Pharmacol, 49: 211-216, 2002; Vogel, et al., Oncology, 61(suppl 2):37-42, 2001; Vogel, et al., Journal of Clinical Oncology, Vol 20, No. 3:719-726, 2002). In addition, several EGFR-targeted therapies are currently under clinical investigation (Mendelsohn, J., & Baselga, J., *Oncogene* 19, 6550-6565 (2000); Xia, W., et al. *Oncogene* 21, 6255-6263 (2002)). In particular, a human anti-EGFr monoclonal antibody, designated ABX-EGF (and also referred to herein as ABX-0303, as described in detail in U.S. Pat. No. 6,235,883; the disclosure of which is hereby incorporated by reference), is being developed by Abgenix, Inc. and Immunex Corporation (Yang X et al. Development of ABX-EGF, a fully human anti-EGF receptor monoclonal antibody, for cancer therapy. Crit Rev Oncol Hemato 38(1):17-23 (2001); Yang X-D et al. Eradication of Established Tumors by a Fully Human Monoclonal Antibody to the Epidermal Growth Factor Receptor without Concomitant Chemotherapy. Cancer Research 59(6): 1236-1243 (1999)).

Historically, cytotoxic cancer therapies have been developed based on maximum tolerated doses (MTD), treating patients without understanding the tumor profile for likely responders. Hence, patients were often subjected to toxic therapies with limited therapeutic benefit. Recently, elucidating tumor growth and survival pathways has led to the development of tumor-targeted therapies. An example of this approach is Gleevec™, an inhibitor of the c-abl family of tyrosine kinases approved for treating chronic myeloid leukemia and gastrointestinal stromal tumors (Druker, B. J. et al., N. Engl. J. Med. 344, 1031-1037 (2001); Demitri, G. D., et al.; *N. Engl. J. Med.* 347, 472-480 (2002)).

In contrast, most erbB-receptor targeted therapies primarily exert cytostatic anti-tumor effects, necessitating their chronic administration. Identification of biologically effective doses (BED), the dose or dose range that maximally inhibits the intended target, beyond which dose escalation is likely to add toxicity without benefit, is therefore essential. Moreover, many of these agents will be used in combination with cytotoxic therapies, where added toxicity may not be tolerable, further supporting BED-based dosing. Targeted-therapy implies that populations of likely responders exists, and can be identified.

In view of the severe and deleterious consequences of administering an inappropriate or ineffective therapy to a human cancer patient, there exists a need in the art for predicting the response to cancer therapy in an individual.

SUMMARY OF THE INVENTION

This invention provides methods for predicting a response of an individual to a particular cancer treatment regimen.

In a first aspect, the invention provides methods for predicting a response to an epidermal growth factor receptor-directed therapy in a human subject, the method comprising the step of assaying a tumor sample from the human subject before therapy with one or a plurality of reagents that detect expression and/or activation of predictive biomarkers for cancer; and determining a pattern of expression and/or activation of at least two of said predictive biomarkers, wherein the pattern predicts the human subject's response to the epidermal growth factor receptor-directed therapy. In certain embodiments, the predictive biomarker is a growth factor receptor, or a growth factor receptor-related downstream signaling molecule. The growth factor receptors can be HER1 (EGFR), pHER1, HER2/neu, HER3, or any combination thereof. The growth factor receptor-related downstream signaling molecules can be pERK. In further embodiments, the predictive biomarkers are HER1 (EGFR), pHER1, HER2/neu, HER3, or pERK, or any combination thereof.

In further embodiments, the predictive biomarkers are HER1 (EGFR) and HER3. In other embodiments, when HER1 (EGFR) is undetectable is predictive of the human subject not responding to the epidermal growth factor receptor-directed therapy. In still other embodiments, wherein when HER3 is undetectable is predictive of the human subject responding to the epidermal growth factor receptor-directed therapy. In further embodiments, the predictive biomarkers are HER1 (EGFR) and pERK; or the predictive biomarkers are pERK and HER3, or the predictive biomarkers are HER1 (EGFR), HER3, and pERK.

In a second aspect, the invention provides a kit for the determining a response to an epidermal growth factor receptor-directed therapy in a subject, wherein the kit comprises at least two reagents that detect expression and/or activation of predictive biomarkers for cancer. In certain embodiments, the kit comprises three reagents. In other embodiments, the predictive biomarkers are HER1, HER3, or pERK, or any combination thereof.

In a third aspect, the invention provides methods for predicting a response to a cancer therapy in a human subject, the method comprising the step of assaying a cell or tissue sample from the human subject before therapy with one or a plurality of reagents that detect expression and/or activation of predictive biomarkers for cancer, wherein said predicative biomarkers consist of growth factor receptor ligands; and determining a pattern of expression and/or activation of at least two of said predictive biomarkers, wherein the pattern predicts the human subject's response to the cancer therapy. In other embodiments, the growth factor receptors are HER1 (EGFR), pHER1, HER2/neu, HER3 or any combination thereof. In still other embodiments, the cancer therapy is an epidermal growth factor receptor-directed therapy. In further embodiments, the cancer therapy is an anti-EGFR antibody. Further, the antibody is ABX-0303.

In a fourth aspect, the invention provides methods of selecting a subject with cancer for treatment with a molecule targeting epidermal growth factor receptor (EGFR), comprising determining the level of expression of HER3 in a cell or tissue sample from the subject, wherein if the level of HER3 expression is low in the cells, the subject is selected. In other embodiments, the molecule is an anti-EGFR antibody. Further, the antibody is ABX-0303. In still other embodiments, the determining step further comprises determining expression of one or more of HER1 (EGFR), pHER1, HER2/neu, and pERK.

In a fifth aspect, the invention provides method of predicting the likely response rate to a molecule targeting epidermal growth factor receptor (EGFR) of a subject having a cancer that overexpresses EGFR, comprising the step of determining the level of expression of HER3 in a cell or tissue sample from the subject, wherein if the level of HER3 expression is low in the cells, the subject is likely to respond to the molecule targeting EGFR. In other embodiments, the molecule is an anti-EGFR antibody. Further, the antibody is ABX-0303. In still other embodiments, the determining step further comprises determining expression of one or more of HER1 (EGFR), pHER1, HER2/neu, and pERK.

In a sixth aspect, the invention provides methods of treating a subject with cancer, comprising determining the level of expression of HER3 in the cells from the subject, and treating the subject with an anti-EGFR antibody when HER3 expression levels in the cell are low. In further embodiments, the antibody is ABX-0303. In other embodiments, the determining step further comprises determining expression of one or more of HER1 (EGFR), pHER1, HER2/neu, and pERK. Further, the antibody is ABX-0303. In still other embodiments, the level of expression of HER3 is undetectable. Further, the antibody is ABX-0303.

In a seventh aspect, the invention provides methods of selecting a subject with cancer for treatment with a molecule targeting epidermal growth factor receptor (EGFR), the method comprising:
  a) determining an expression and/or activation profile of two or more growth factor receptors in cells and/or tissues of the subject; and
  b) selecting the subject based on the expression and/or activation profile, wherein the subject is selected when the level of expression of HER3 is low, the level of expression of the HER1 is high, and/or the level of the pERK index is high. In other embodiments, the molecule is an anti-EGFR antibody. Further, the antibody is ABX-0303. In another aspect, the growth factor receptors comprise one or more of HER1 (EGFR), pHER1, HER2/neu, and HER3.

Specific embodiments of the present invention will become evident from the following more detailed description of certain preferred embodiments and the claims.

DETAILED DESCRIPTION OF PREFERRED EMBODIMENTS

Figure 1:
FIG. 1 illustrates the response to ABX-0303 by a patient with elevated HER1 and pERK, and decreased levels of HER3. The figure represents quantitative immunohistochemical analysis of EGFR, pEGFR, HER2, HER3, and pERK.
Figure 1:
Figure 1:
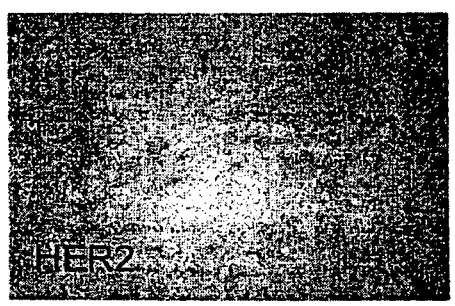
Figure 1:
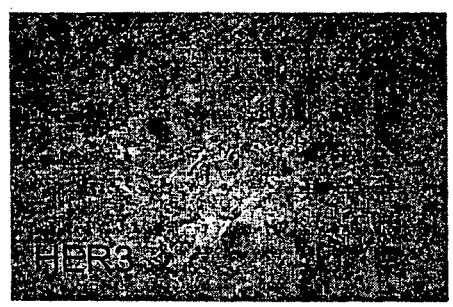
Figure 1:

This invention provides methods for predicting response in cancer subjects to cancer therapy, including human cancer patients.

In contrast to traditional anticancer methods, where chemotherapeutic drug treatment is undertaken as an adjunct to and after surgical intervention, neoadjuvant (or primary) chemotherapy consists of administering drugs as an initial treatment in cancer patients. One advantage of such an approach is that, for primary tumors of more than 3 cm, it permits the use of conservative surgical procedures (as opposed to, e.g., radical mastectomy in breast cancer patients) for the majority of patients, due to the tumor-shrinking effect of the chemotherapy. Another advantage is that for many cancers, a partial and/or complete response is achieved in about two-thirds of all cases. Finally, because the majority of patients are responsive after two to three cycles of chemotherapeutic treatment, it is possible to monitor the in vivo efficacy of the chemotherapeutic regimen employed, which is important for a timely identification of those cancers which are non-responsive to chemotherapeutic treatment. Timely identification of non-responsive tumors, in turn, allows the clinician to limit the cancer patient's exposure to unnecessary side-effects of treatment and to institute alternative treatments. However, the methods present in the art, including histological examination, are insufficient for such a timely and accurate identification. The present invention provides methods by which a more informed and effective regime of therapy can be administered.

A cancer diagnosis, both an initial diagnosis of disease and subsequent monitoring of the disease course (before, during, or after treatment) is conventionally confirmed through histological examination of cell or tissue samples removed from a patient. Clinical pathologists need to be able to accurately determine whether such samples are benign or malignant and to classify the aggressiveness of tumor samples deemed to be malignant, because these determinations often form the basis for selecting a suitable course of patient treatment. Similarly, the pathologist needs to be able to detect the extent to which a cancer has grown or gone into remission, particularly as a result of or consequent to treatment, most particularly treatment with chemotherapeutic or biological agents.

Histological examination traditionally entails tissue-staining procedures that permit morphological features of a sample to be readily observed under a light microscope. A pathologist, after examining the stained sample, typically makes a qualitative determination of whether the tumor sample is malignant. It is difficult, however, to ascertain a tumor's aggressiveness merely through histological examination of the sample, because a tumor's aggressiveness is often a result of the biochemistry of the cells within the tumor, such as protein expression or suppression and protein activation, which may or may not be reflected by the morphology of the sample. Therefore, it is important to be able to assess the biochemistry of the cells within a tumor sample. Further, it is desirable to observe and quantitate both gene expression and protein activation of tumor related genes or proteins, or more specifically cellular components of a tumor-related signally pathway.

Cancer therapy can be based on molecular profiling of tumors rather than histology or site of disease. Elucidating the biological effects of targeted-therapies in tumor tissue and correlating these effects with clinical response helps identify the predominant growth and survival pathways operative in tumors, thereby establishing a profile of likely responders and conversely providing a rational for designing strategies to overcoming resistance.

It is necessary to consider additional biomarkers beyond the presence of the target, such as EGFR, for subjects who are considered for treatment with, for example, biomolecules that modulate EGFR. Not all tumor cells respond to inhibition of ErbB receptors, despite exhibiting aberrant ErbB-1 and/or ErbB-2 expression. Examples include MKN7 and BT474

ErbB receptor-overexpressing carcinoma cell lines, wherein BT474 cells respond to HERCEPTIN® but MKN7 cells do not. These observations have clear implications for erbB-directed therapeutics and the consideration of the expression of multiple erbB receptors and in tumors.

For example, ABX-0303 (as referred to herein as ABX-EGF), an epidermal growth factor receptor-directed therapy sponsored by Abgenix and Immnunex Corporation, effectively targets HER1 to prevent the growth of renal cell cancers. Based on the positive correlation between pERK expression and response to ABX-0303, it is likely that HER1 is acting through the MAPK pathway. In addition, HER3 was found to be elevated in a large percentage of renal biopsies analyzed from non-responders. One possibility is that HER3 is interacting with HER2 to confound the action of the drug.

Automated (computer-aided) image analysis systems known in the art can augment visual examination of samples. In a representative system, the cell or tissue sample is exposed to detectably labeled reagents specific for a particular biological marker, and the magnified image of the cell is then processed by a computer that receives the image from a charge-coupled device (CCD) or camera such as a television camera. Such a system can be used, for example, to detect and measure expression and activation levels of Her1, pHER1 HER2, HER3, and pERK in a sample. Additional biomarkers are also contemplated by this invention. This methodology provides more accurate diagnosis of cancer and a better characterization of gene expression in histologically identified cancer cells, most particularly with regard to expression of tumor marker genes or genes known to be expressed in particular cancer types and subtypes (i.e., different degrees of malignancy). This information permits a more informed and effective regimen of therapy to be administered, because drugs with clinical efficacy for certain tumor types or subtypes can be administered to patients whose cells are so identified.

For example, expression and activation of proteins expressed from tumor-related genes can be detected and quantitated using methods of the present invention. Further, expression and activation of proteins that are cellular components of a tumor-related signaling pathway can be detected and quantitated using methods of the present invention. Further, proteins associated with cancer can be quantified by image analysis using a suitable primary antibody against biomarkers, such as, but not limited to, Her-1, Her-2, p-Her-1, Her-3, or p-ERK, and a secondary antibody (such as rabbit anti-mouse IgG when using mouse primary antibodies) and/or a tertiary avidin (or Strepavidin) biotin complex ("ABC").

In practicing the method of the present invention, staining procedures can be carried out by a technician in the laboratory. Alternatively, the staining procedures can be carried out using automated systems. In either case, staining procedures for use according to the methods of this invention are performed according to standard techniques and protocols well-established in the art.

By "cell or tissue sample" is meant biological samples comprising cells, most preferably tumor cells, that are isolated from body samples, such as, but not limited to, smears, sputum, biopsies, secretions, cerebrospinal fluid, bile, blood, lymph fluid, urine and faeces, or tissue which has been removed from organs, such as breast, lung, intestine, skin, cervix, prostate, and stomach. For example, a tissue sample can comprise a region of functionally related cells or adjacent cells.

The amount of target protein can then be quantitated by the average optical density of the stained antigens. Also, the proportion or percentage of total tissue area stained may be readily calculated, as the area stained above an antibody threshold level in the second image. Following visualization of nuclei containing biomarkers, the percentage or amount of such cells in tissue derived from patients after treatment may be compared to the percentage or amount of such cells in untreated tissue or said tissue prior to treatment. For purposes of the invention herein, "determining" a pattern of expression and/or activation of a biomarker is understood broadly to mean merely obtaining the information on such biomarker(s), either through direct examination or indirectly from, for example, a contract diagnostic service.

Thus, the level of expression and/or activation in a cell can be determined by, for example, quantitative immunohistochemistry. In this case, the level of expression of HER1, HER2, and/or HER3 is considered to be low if the OD is less than 9. Further, the level of expression is also considered to be low if the OD is less than 5, or less than 3, or if the OD is 0 (undetectable). In addition, the level of expression of HER1, HER2, and/or HER3 is considered to be high is the OD is greater than 9. Further, the level of expression can be considered high for pERK when the pERK index is greater than 99.

Particularly useful embodiments of the present invention and the advantages thereof can be understood by referring to Examples 1-7. These Examples are illustrative of specific embodiments of the invention, and various uses thereof. They are set forth for explanatory purposes only, and are not to be taken as limiting the invention.

EXAMPLE 1

Staining Procedure for Biomarkers

Human tumor tissue samples were stained as follows. Tumor tissue in 10% Neutral Buffered Formalin Paraffin blocks are sectioned at 4 microns and the sections placed onto coated slides. EGFR immunostaining is preformed by using Ventana Medical Instruments, Inc. monoclonal 111.6; HER-2 immunostaining is performed by using Ventana Medical Instruments, Inc. monoclonal CB11, and HER-3 immunostaining is performed by using Ventana Medical Instruments, Inc. monoclonal SGP1. Her-1, Her-2, and Her-3 are immunostained using, for example, the "BenchMark" (VMSI) with I-VIEW (VMSI) detection chemistry. pEGFR immunostaining is performed by using Chemicon monoclonal MB3052. p-ERK (1:100) is obtained from Cell Signaling Technology (Beverly, Mass.) and immunostained using a labeled streptavidin peroxidase technique.

For example, slides for p-ERK (1:100) are antigen retrieved using 0.1 M citrate buffer, pH 6.0 in the "decloaker" (Biocare Corp.) and the sections incubated overnight with the primaries at 4° C. The next day, the slides for pERK and pAKT are placed onto the Autostainer (Dako Corp.) and the "LSAB2" kit (Dako) is employed as the detection chemistry. DAB (Dako) is used as the chromogen. After immunostaining, all immunomarkers, are counterstained manually with 4% ethyl green (Sigma).

EXAMPLE 2

Procedure for Immunohistochemistry

Quantitative immunohistochemistry (IHC) is performed as previously described (Bacus, S., et al., *Analyt. Quant. Cytol. Histol.* 19, 316-328 (1997)). EGFR, and erbB-2 immunostaining is performed using the pre-diluted EGFR (Ventana monoclonal 111.6) and erbB-2 (Ventana monoclonal CB11) antibodies from Ventana on the VMSI automated "BenchMark" staining module as described. The VMSI "I-View"

detection kit is used for all of the VMSI pre-diluted primary antibodies. HER-3 is also immunostained using the "Bench-Mark" with I-VIEW detection chemistry. pErk is immunostained using a labeled streptavidin peroxidase technique. Phospho-Erk1/2 slides are antigen retrieved as described (Bacus, S., et al., *Analyt. Quant Cytol. Histol.* 19, 316-328 (1997)). Slides are placed onto the Autostainer (Dako Corp.) and the "LSAB2" kit (Dako) employed as the detection chemistry. pEGFR is immunostained in a similar labeled streptavidin peroxidase technique. pEGFR slides are antigen retrieved with 1 mM EDTA and slides for p-erbB-2 with 0.1 M citrate buffer, pH 6.0, in the "decloaker". After staining, EGFR, HER2, HER3, pErk, and pEGFR, are counterstained manually with 4% ethyl green (Sigma). TUNEL assay (Roche Diagnostics, Indianapolis) is performed according to the manufacturer's instructions. Investigators preparing and analyzing tissue sections are blinded to both patient tumor type and response to therapy.

For IHC, antibodies to EGFR, HER2 and HER3 were from Ventana Medical Scientific Instruments (VMSI) (Tucson, Ariz.); pERK was from Cell Signaling Technology Inc. (Beverly, Mass.); anti pEGFR and from Chemicon (Temecula, Calif.).

EXAMPLE 3

Analysis of Treatment with an Epidermal Growth Factor-Directed Therapy 53 samples from renal cancer patients enrolled in a clinical trial sponsored by Abgenix and Immunex Corporation for an investigational drug directed to EGFR were analyzed for expression of various biomarkers. The sample slides were obtained from Impath Laboratories, Inc.

Immunohistochemical (IHC) analyses were carried out using the automated staining devices as described above. The antibodies used for the specific biomarkers included: Ventana monoclonal 111.6 for EGFR, Chemicon monoclonal MB3052 for pEGFR, polyclonal pERK from Cell Signaling Technology for pERK, Ventana monoclonal SGP1 for HER3, and Ventana monoclonal CB11 for HER2. For each specimen, a slide was stained with control mouse immunoglobulins to establish the existence and localization of background staining. In addition, appropriate positive controls were run for each IHC stain. Following counterstaining with ethyl green, the slides were permanently mounted and analyzed using interactive image analysis to establish the optical density of peroxidase stained cytoplasmic and membrane staining. In the case of pERK, the fraction of cells expressing nuclear pERK, and the intensity of the stain were measured using a CAS system, and the results were expressed as the pERK index (product of OD x percent positive nuclear area). The technician quantifying the results observed areas of tumor that were not adjacent to normal renal tubules to avoid confounding the quantification. In all cases, the stained slides were viewed by at least two people, including a pathologist and a senior scientist, to establish that the quantification results were representative of the stained sections.

Immunohistochemical analyses, quantification, and correlation with response data were completed for twenty-nine (29) of the specimens. Partial data, representing analysis of only a subset of the selected biomarkers, was available for an additional twelve (12) samples. No data was obtained on the remaining specimens because of questions as to the identity of the slides, or the absence of information concerning the patient's response to ABX-0303. The conclusions that can be drawn from the analysis include, but are not limited to, that response to ABX-0303 is related to the expression of HER1, and that elevated expression of HER3 compromises the action of the drug.

Results of the IHC analysis of the renal cancer biopsies, for which at least HER1 IHC results and clinical response information was available, is presented in Table 1.

TABLE I

IHC ANALYSIS

| Pt # | HER1 | HER1 "score" | pHER1 | pERK Index | HER3-st | HER2-st | HER2 cocktail | Treatment Group | Histologic Type | Response |
|---|---|---|---|---|---|---|---|---|---|---|
| 3001 | 8 | 0 | | 36 | 17 | 3 | | 1.0 mg/kg | Clear Cell Carcinoma | PD |
| 3002 | 19 | +2 | 20 | 7 | 27 | 5 | +2 | 1.0 mg/kg | Clear Cell Carcinoma | S |
| 3003 | 8 | | 2 | | | | | 1.0 mg/kg | Other | MR |
| 3006 | 6 | +1 | 0 | 896 | 32 | 0 | +1 (focal) | | Clear Cell Carcinoma | PD |
| 3007 | 18 | +2 | 6 | 1127 | 27 | 0 | 0 | 1.0 mg/kg | Clear Cell Carcinoma | S |
| 3008 | 19 | +2 | 0 | 12 | 15 | 3 | | 1.0 mg/kg | Clear Cell Carcinoma | PD |
| 3009 | 0 | +2 (focal) | 0 | 96 | 15 | 0 | 0 | 1.0 mg/kg | Clear Cell Carcinoma | PD |
| 3010 | 21 | +3 | 0 | 1100 | 33 | 10 | | | | PD |
| 3011 | 5 | | 0 | | | | | 1.0 mg/kg | Clear Cell Carcinoma | S |
| 3012 | 8 | +1 | 3 | 40 | 15 | 1 | 0 | 1.0 mg/kg | Clear Cell Carcinoma | S |
| 3014 | 17 | +2 to +3 | | 132 | 0 | | | 1.0 mg/kg | Other | S |
| 3018 | 20 | +3 | 9 | 90 | 16 | 0 | 0 | 1.0 mg/kg | Papillary Carcinoma | PD |
| 3019 | 18 | +2 | 14 | 924 | 2 | 0 | | 1.0 mg/kg | Other | PR |
| 3020 | 10 | +3 | 3 | 1176 | 14 | 13 | | 1.0 mg/kg | Clear Cell Carcinoma | S |
| 3031 | 0 | 0 | 5 | 0 | 0 | 0 | +1 | 1.5 mg/kg | Clear Cell Carcinoma | PD |
| 3032 | 0 | +1 (very weak) | 1 | 99 | 2 | 0 | +1 | 1.5 mg/kg | Clear Cell Carcinoma | S |
| 3033 | 18 | +2 to +3 | 14 | 390 | 50 | 2 | +2 | | | PD |
| 3036 | 4 | +1 | 0 | 540 | 0 | 0 | +1 | | | S |
| 3037 | 8 | | | | | | | 1.5 mg/kg | Clear Cell Carcinoma | S |
| 3039 | 16 | +2 | 0 | 208 | 21 | | | 1.5 mg/kg | Clear Cell Carcinoma | S |
| 3043 | 15 | +2 | 0 | 143 | 40 | 0 | +2 | 1.5 mg/kg | Papillary Carcinoma | PD |
| 3047 | 11 | +1 to +2 (focal) | 0 | 64 | 37 | 0 | +1 | 1.5 mg/kg | Clear Cell Carcinoma | S |
| 3051 | 18 | +2 | 5 | 247 | | | | 1.5 mg/kg | Clear Cell Carcinoma | S |

TABLE I-continued

IHC ANALYSIS

| Pt # | HER1 | HER1 "score" | pHER1 | pERK Index | HER3-st | HER2-st | HER2 cocktail | Treatment Group | Histologic Type | Response |
|---|---|---|---|---|---|---|---|---|---|---|
| 3053 | 7 | +1 | 26 | 0 | 45 | 2 | | 1.5 mg/kg | Other | PD |
| 3065 | 23 | +3 | 15 | 108 | 22 | | | 2.0 mg/kg | Clear Cell Carcinoma | S |
| 3068 | 16 | +2 | 10 | 221 | 4 | 9 | +1 | 2.0 mg/kg | Clear Cell Carcinoma | S |
| 3070 | 33 | +3 | 0 | 465 | 38 | 15 | | 2.0 mg/kg | Clear Cell Carcinoma | PD |
| 3073 | 2 | 0 | 0 | 126 | 23 | 0 | | 2.0 mg/kg | Papillary Carcinoma | PD |
| 3075 | 22 | +3 | 4 | 77 | 28 | 13 | | 2.0 mg/kg | Clear Cell Carcinoma | PD |
| 3077 | 25 | | 0 | | | | | 2.0 mg/kg | Clear Cell Carcinoma | S |
| 3078 | 6 | 0 | 1 | 90 | 11 | | | 2.0 mg/kg | Clear Cell Carcinoma | PD |
| 3080 | 8 | +1 (weak) | 21 | 8 | 44 | 11 | | 2.0 mg/kg | Clear Cell Carcinoma | PD |
| 3084 | 20 | +3 | 0 | 8 | 34 | 5 | | 2.0 mg/kg | Clear Cell Carcinoma | S |
| 3092 | 6 | +1 | 5 | 576 | | | | 2.5 mg/kg | Clear Cell Carcinoma | S |
| 3095 | 10 | +1 | 1 | 0 | 9 | 0 | +2 | | | MR |
| 3099 | 13 | +2 | 34 | 90 | 13 | 6 | | 2.5 mg/kg | Clear Cell Carcinoma | S |
| 3101 | 11 | +2 to +3 | 0 | 6 | 25 | 0 | 0 | 2.5 mg/kg | Other | PD |
| 3103 | 20 | +3 | 0 | 1134 | 30 | 5 | +2 | 2.5 mg/kg | Clear Cell Carcinoma | PD |
| 3105 | 15 | | | | | | | 2.5 mg/kg | Papillary Carcinoma | PD |
| 3108 | 11 | | | | | | | 2.5 mg/kg | Clear Cell Carcinoma | S |

Results are presented as OD unless otherwise indicated

Based on this analysis, in which the positive and negative predictive values were calculated as a function of the optical density, or fraction positivity, values were determined to stratify samples based upon expression of the biomarkers analyzed. The results of the analysis of using these stratification criteria is presented in Table II.

TABLE II

DATA ANALYSIS

| group of samples (n) | RESPONDERS | NONRESPONDERS |
|---|---|---|
| all reported in study (41) | 56% | 44% |
| HER1 OD > 9 (25) | 60% | 40% |
| HER1 OD < 10 (16) | 44% | 56% |
| HER1 visual score of +1 or greater (30) | 60% | 40% |
| pERK index > 99 (19) | 63% | 37% |
| pERK index < 100 (16) | 38% | 62% |
| HER1+/perk– (8)* | 50% | 50% |
| HER1+/perk+ (12) | 64% | 36% |
| HER3 OD > 9 (26) | 38% | 62% |
| HER3 OD < 10 (7) | 86% | 14% |
| HER3+/HER1+ (17) | 47% | 53% |
| HER3+HER1– (9) | 22% | 78% |
| HER3+/perk+ (13) | 46% | 54% |
| HER3+/perk– (13) | 31% | 69% |
| HER2 OD > 9 (6) | 33% | 67% |
| HER2 OD < 10 (23) | 48% | 52% |

*for purposes of this analysis "+" refers to OD greater than 9 upon quantification of HER1, HER2, or HER3; or pERK index of greater than 99.

Overall, there was no single marker that, when quantified, absolutely correlated with response to ABX-0303. This data indicates, however, that expression of HER1 and pERK predict response to the drug, while samples expressing HER3 are less likely to respond well. The quantitative analysis presented assumes that any expression of these markers that gives an optical density reading of 10 or greater was significant. It is interesting to note that visual assessment of HER1 staining, where any intensity of 1+ or greater is considered positive, agrees with the quantification of this marker. Also of interest, only three of the thirty-three samples examined by a pathologist were scored as "0" for HER1 staining intensity, and all three samples were from patients who failed to respond to ABX-0303. Thus, the absence of detectable HER1 (staining intensity "0"), can also be a predictor of response to ABX-0303.

The presence of HER3 seems to be a negative predictor of response. Patients whose specimens lacked HER3 by the criterion used here were more likely to respond than those that had HER3 (86% vs. 38%). There was no significant correlation between the presence of the phosphorylated form of HER1 and response to ABX-0303. The lack of pHER1 expression, however, even in samples with significantly elevated levels of HER1, may have been a result of a failure to preserve the phosphorylated form of this protein during the collection and processing of biopsies. Only 6 of the samples analyzed by quantitative IHC were HER2 "positive" by the criterion of having on OD of 10 or greater. As shown in Table II, these were predominantly poor responders to the drug. Interestingly, all six of these samples had elevated levels of HER3. HER2 expression, quantified using a monoclonal antibody directed against the external domain of HER2, was further determined using a cocktail of antibodies that recognize both the internal and external domains of the protein. While some additional samples appeared to be positive using this alternate approach, these observations were not sufficient to confirm the correlation between HER2 and HER3 expression with lack of response to ABX-0303.

Figure 2:
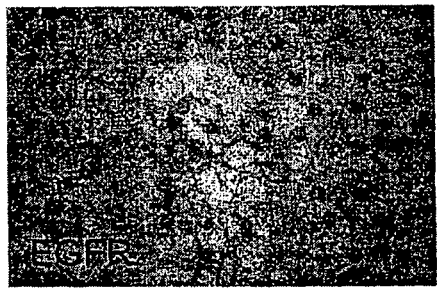
FIG. 2 illustrates the response to ABX-0303 by a patient with elevated HER1, HER3, and pERK. The figure represents quantitative immunohistochemical analysis of EGFR, pEGFR, HER2, HER3, and pERK.
Figure 2:
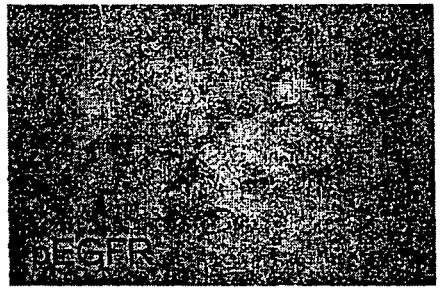
Figure 2:
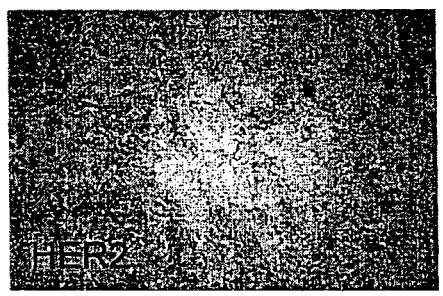
Figure 2:
Figure 2:

The expression and co-expression of HER1, HER3, and pERK indicates that HER1, acting through pERK, was critical to ABX-0303 response, and that the action of the drug is compromised in some manner by the presence of HER3. Notably, biopsies that showed HER3 but not HER1 expression were less likely to respond to ABX-0303 (22% response rate) than patients whose tumors expressed both proteins (47% response rate). Dramatically, samples from patients that had low levels of HER3 but expressed HER1 and/or pERK at levels of greater than 9, had a 100% response rate to ABX-0303. An analysis with a greater number of samples will help confirm any of the conclusions drawn from this analysis. Examples of tumors with high and low levels of HER3 are provided in FIGS. 1 and 2.

This data indicates that ABX-0303 effectively targets HER1 to prevent the growth of renal cell cancers. It is not surprising that HER1 seems to be acting through the MAPK pathway, as shown by the positive correlation between pERK expression and response. Of interest is the role of HER3, which was found elevated in 79% of the renal biopsies analyzed.

As will be appreciated, the above findings provide useful methods for the selection of patients for treatment with molecules that target EGFR and predictors of the response of patients. In addition, the above findings provide useful methods for the use of ABX-0303. ABX-0303 is described in detail in U.S. Pat. No. 6,235,883 (the disclosure of which is hereby incorporated by reference) and referred to therein in connection with the discussions related to hybridoma E7.6.3.

It should be understood that the foregoing disclosure emphasizes certain specific embodiments of the invention and that all modifications or alternatives equivalent thereto are within the spirit and scope of the invention as set forth in the appended claims. All references discussed herein are hereby incorporated by reference in their entirety.

What we claim is:

1. A method for predicting a response to epidermal growth factor receptor-directed therapy in a human subject, the method comprising the step of assaying a tumor sample from a candidate human subject for epidermal growth factor receptor-directed therapy with a plurality of reagents that detect expression and/or activation of predictive biomarkers for cancer; detecting expression of said plurality of predictive biomarkers to produce a pattern of expression and/or activation of a least two of said predictive biomarkers, and predicting a response to an epidermal growth factor receptor-directed therapy using the detected pattern of expression and/or activation of at least two predictive biomarkers, wherein the predictive biomarkers are selected from the group consisting of a growth factor receptor and a growth factor receptor-related downstream signaling molecule; and wherein the growth factor receptor is HER-1 (EGFR) and/or HER-3, and the growth factor receptor-related downstream signaling molecule is pERK.

2. The method of claim 1, where in the predictive biomarkers are HER-1 (EGFR) and HER-3.

3. The method of claim 2, wherein undetectable expression of HER-1 (EGFR) is predictive of the human subject not responding to the epidermal growth factor receptor-directed therapy.

4. The method of claim 2, wherein undetectable expression of HER-3 is predictive of the human subject responding to the epidermal growth factor receptor-directed therapy.

5. The method of claim 1, where in the predictive biomarkers are HER-1 (EGFR) and pERK.

6. The method of claim 1, where in the predictive biomarkers are pERK and HER-3.

7. The method of claim 1, where in the predictive biomarkers are HER-1 (EGFR), HER-3, and pERK.

8. A method of predicting the response rate of a subject having a cancer that overexpresses EGFR to a molecule targeting epidermal growth factor receptor (EGFR), comprising assaying a cell or tissue sample from said subject for at least two predictive biomarkers, wherein the predictive biomarkers are HER-3, HER-1 and pERK, wherein the assay detects expression levels of the at least two biomarkers; and predicting the response to an epidermal growth factor receptor-directed therapy; wherein undetectable expression of HER-1 (EGFR) is predictive of the subject not responding to the epidermal growth factor receptor-directed therapy; wherein undetectable expression of HER-3 is predictive of the subject responding to the epidermal growth factor receptor-directed therapy; and wherein undetectable expression of pERK is predictive of the subject not responding to the epidermal growth factor receptor-directed therapy.

9. The method of claim 8, wherein the molecule is an anti-EGFR antibody.

10. The method of claim 9, wherein the antibody is ABX-0303.

11. A method of selecting a subject with cancer for treatment with a molecule targeting epidermal growth factor receptor (EGFR), the method comprising: a) assaying a cell or tissue sample from said subject for at least two predictive biomarkers, wherein the predictive biomarkers are HER-3, HER-1 and/or pERK, wherein the assay detects expression levels of the at least two biomarkers; predicting the response to an epidermal growth factor receptor-directed therapy; and selecting the subject for treatment with the molecule when the expression level of the at least two predictive biomarkers is selected from the group consisting of detectable expression of HER-1 (EGFR), undetectable expression of HER-3, and detectable expression of pERK.

12. The method of claim 11, wherein the molecule is an anti-EGFR antibody.

13. The method of claim 12, wherein the antibody is ABX-0303.

14. The method of claim 11, wherein the subject is selected for treatment with the molecule when the expression level of HER-3 is undetectable, when the HER-1 expression level is detectable, and when the pERK expression level is detectable.

* * * * *